(12) United States Patent
Elnatan et al.

(10) Patent No.: US 6,931,949 B2
(45) Date of Patent: Aug. 23, 2005

(54) APPARATUS FOR MEASURING THE WEIGHT OF SMALL ITEMS

(75) Inventors: Ehud Elnatan, Jerusalem (IL); Yuval Lichi, Jerusalem (IL); Yossi Shomer, East Binyamin (IL); Shay Popper, Tzoren (IL)

(73) Assignee: D.A.T.A. Diamond Advanced Technology Ltd., Jerusalem (IL)

( * ) Notice: Subject to any disclaimer, the term of this patent is extended or adjusted under 35 U.S.C. 154(b) by 143 days.

(21) Appl. No.: 10/670,506

(22) Filed: Sep. 26, 2003

(65) Prior Publication Data

US 2005/0016301 A1 Jan. 27, 2005

(30) Foreign Application Priority Data

Sep. 29, 2002 (IL) .................................. 151994
Dec. 19, 2002 (IL) .................................. 153544

(51) Int. Cl.$^7$ ...................... G01G 11/00; G01G 11/04; G01G 3/16; G01M 7/00; G01N 29/00
(52) U.S. Cl. ...................... 73/865; 73/580; 177/210 FP
(58) Field of Search .............. 73/580, 865; 177/210 FP

(56) References Cited

U.S. PATENT DOCUMENTS

| | | | |
|---|---|---|---|
| 3,595,329 A | 7/1971 | Withnell et al. | ........ 177/210 R |
| 4,623,030 A | 11/1986 | Portman, Jr. et al. | .. 177/210 FP |
| 4,845,656 A | 7/1989 | Nishibe et al. | ............. 345/562 |
| 6,397,678 B1 | 6/2002 | Popper | ........................ 73/580 |
| 6,668,652 B2 * | 12/2003 | Nakayama et al. | ........... 73/580 |

* cited by examiner

*Primary Examiner*—Hezron Williams
*Assistant Examiner*—Tamiko Bellamy
(74) *Attorney, Agent, or Firm*—Foley & Lardner LLP

(57) ABSTRACT

The invention provides an apparatus for measuring the mass and calculating the weight of individual objects to be held thereby, comprising forceps having a proximal portion and a distal portion, the proximal portion being adapted to grasp and hold a selected object, means associated with the forceps for initiating vibration of the same while the object is held thereby and means for measuring the oscillating frequency of the forceps while the object is held thereby, and for utilizing the measured higher oscillating frequency of the empty forceps to compute the mass and the weight of the selected object.

15 Claims, 4 Drawing Sheets

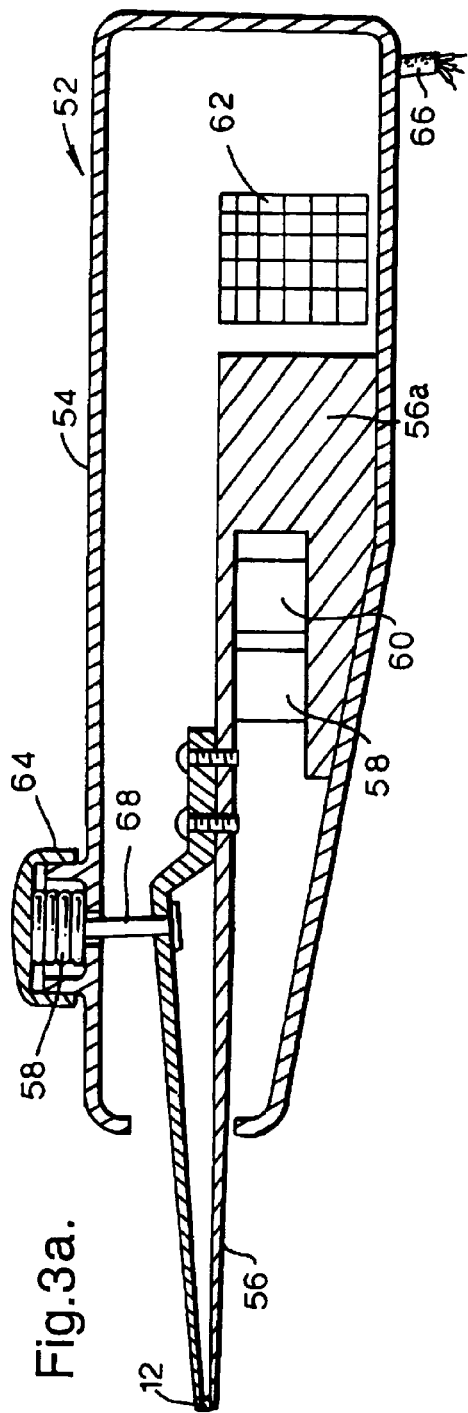
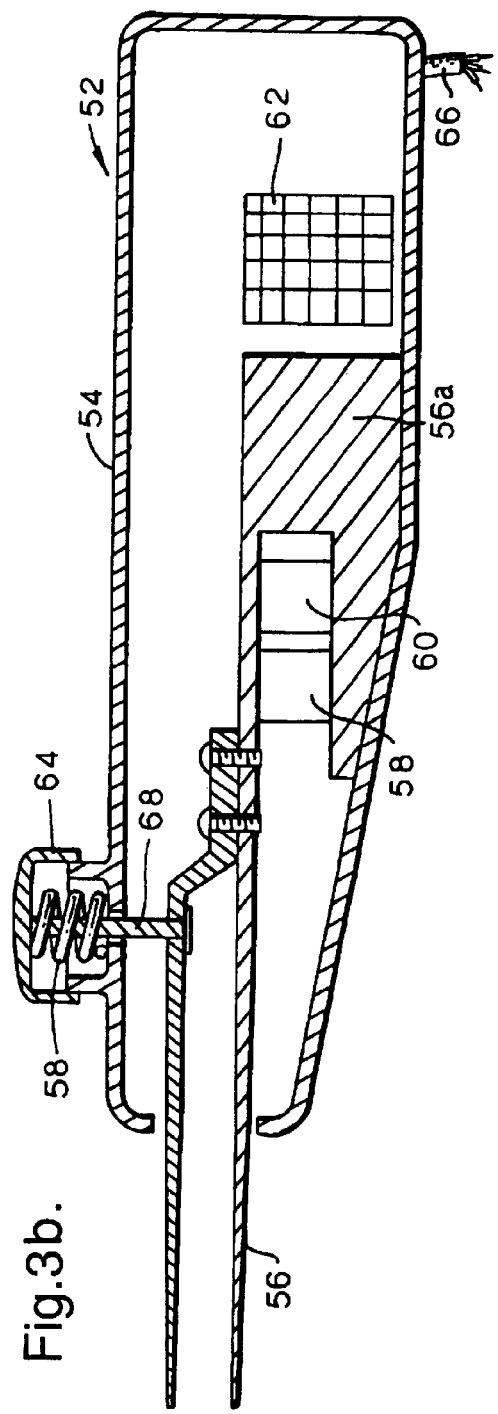

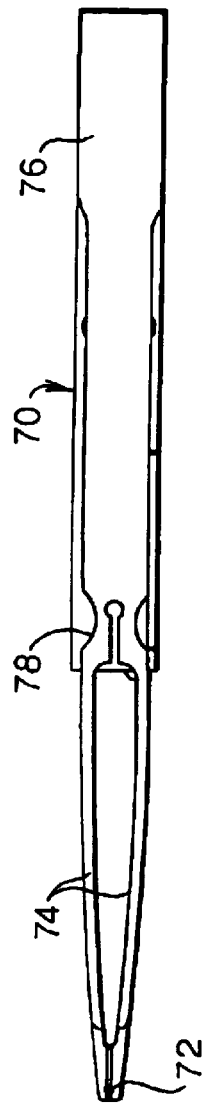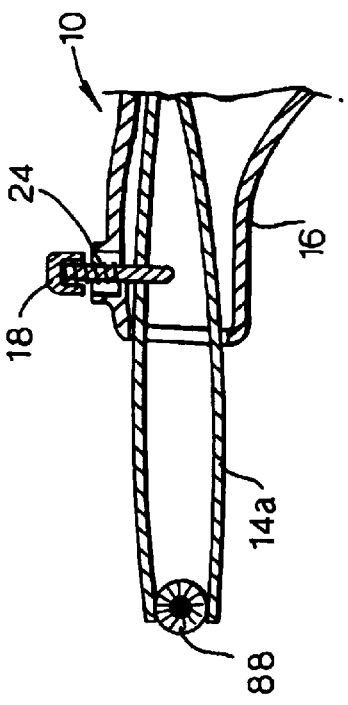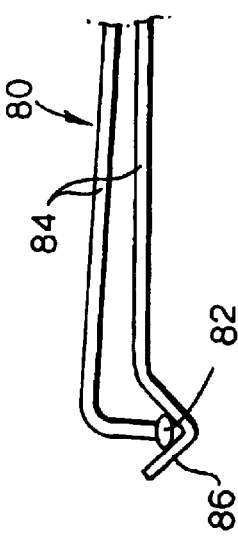

APPARATUS FOR MEASURING THE WEIGHT OF SMALL ITEMS

The present invention relates to the weighing of small items.

More particularly, the present invention provides an apparatus for determining the weight of a small object, by comparing the vibration or oscillating frequency of forceps while said object is being held thereby with the oscillating frequency of the empty forceps when vibrating without an object held thereby. The apparatus of the present invention is primarily intended for weighing gemstones, small items made of precious metals and diamonds.

In the following text, the word "stone" is to be interpreted as either a gemstone or a diamond, whether polished or in the rough state.

Known equipment for weighing stones or size sorting include mechanical dish scales with a set of weights, which though slow and cumbersome are still being marketed.

Rough diamonds can be sorted by a series of disks having a multitude of accurate holes, as seen for example in Israel Patent No. 119 867.

A large variety of electronic scales are commercially available for weighing stones. A catalogue entitled "Supplies and Instruments for the Diamond and Jewelry Trade" by Rubin and Son, Antwerp, Belgium features a range of battery-operated portable digital scales, some small enough to be carried in the pocket. Accuracy of the scales is dependent on the total range covered. For a maximum capacity scale of 50 gram accuracy claimed is 0.1 gram. Scales of 1200 gram capacity have an accuracy of 5 gram. Such accuracy is acceptable where many stones are being weighed together. For a single small stone such accuracy is unlikely to suffice.

Marquis et al. in U.S. Pat. No. 4,845,646 disclose a device which measures the size of a stone, relates to a user input regarding the shape of the stone, and on this basis calculates the weight. Clearly there is room for error in the result calculated, as neither the depth nor the density of the stone is considered.

When a mass is set in vibration while supported in a flexible manner, the frequency of vibration remains unchanged whether the initial displacement is larger or smaller, whether the system is highly or lightly damped. However any increase in the mass being supported reduces the frequency of vibration. Significantly for the purpose of the present invention, the relationship is of the type expressed by the following statement:

Frequency is proportional to a factor/mass ½.

Thus, frequency is very sensitive to changes in mass. By squaring both sides, it becomes clear that frequency squared is inversely related to the mass. It follows that if mass is increased, for example, by a factor of 3, frequency will decrease by a factor of 9. Thus the advantage of frequency measurement as a basis for mass measurement is readily understood.

All devices using inertia-type mechanisms produce results measured in mass units, while manufacturers dealers and buyers are interested in the weight of the stone (in grams, ounces, carats or points) and not its mass. Assuming that all practical measurements will be made at locations having the same acceleration due to gravity, weight can be taken to be directly proportional to mass and can be easily and automatically calculated therefrom.

Withnell et al. in U.S. Pat. No. 3,595,329 disclose a weighing device for checking the weight of a tablet relative to a reference tablet. The inertia of the tablet being checked is deduced from the amplitude of vibration resulting from energy imparted by an electromechanical vibrator. There is no frequency measurement.

The ratio weighing device disclosed by Portman, Jr. Et al in U.S. Pat. No. 4,623,030 uses a piezoelectric driver and receiver to determine the weight change in a sample after part of the sample is removed. The vibration device is operated by comparing two AC outputs from the receiver, and is said to be useful for determining the carbon residue in a drop of a petroleum product weighed before and after heating.

The advantages of frequency measurement are utilized by Popper in U.S. Pat. No. 6,397,678 B1, who discloses a method for measuring objects, particularly diamonds. This disclosure will again be referred to further on.

It is therefore one of the objects of the present invention to obviate the limitations of prior art weighing devices for small objects and to provide a device which uses frequency measurements of a vibrating holder to improve accuracy of the results.

It is a further object of the present invention to provide a weighing device which reliably holds small stones of any shape or size.

Yet a further object of the present invention is to provide a fully portable device which can be used anywhere and is independent of outside service supplies such as electric power or vacuum.

The present invention achieves the above objects by providing an apparatus for measuring the mass and calculating the weight of individual objects to be held thereby, comprising forceps having a proximal portion and a distal portion, said proximal portion being adapted to grasp and hold a selected object, means associated with said forceps for initiating vibration of the same while said object is held thereby and means for measuring the oscillating frequency of said forceps while said object is held thereby, and for utilizing the measured higher oscillating frequency of the empty forceps to compute the mass and the weight of said selected object.

In a preferred embodiment of the present invention there is provided an apparatus for measuring the mass and calculating the weight of objects, wherein means for measuring the oscillating frequency of said forceps include optical means such as a light emitter, a light detector and a plurality of optical fibers adapted to transfer light to the vibrating forceps and to transfer collected light inputs to said detector.

In a most preferred embodiment of the present invention there is provided an apparatus for measuring the mass and calculating the weight of objects, wherein said forceps, said means for initiating vibration thereof and said means for measuring the oscillating frequency of said forceps while said object is held thereby are all contained in a unitary hand-holdable housing further comprising display means for showing the computed weight of said object held thereby.

Especially preferred are embodiments wherein the vibration of the forceps is initiated by application of a momentary electric pulse applied to a solenoid causing the solenoid plunger to strike the forceps.

Yet further embodiments of the invention will be described hereinafter.

In U.S. Pat. No. 6,397,678 B1 Popper discloses a method and apparatus for measuring objects, particularly diamonds, which are to be held on a vibrating probe end by means of vacuum. The device is said to be capable of high speed operation.

As the stones to be weighed are of irregular shape, the reliability of the pick-up is doubtful. For example, if the probe contacts a concave or irregular surface, there will be air leakage causing failure to grasp the object to be weighed. Furthermore, it is difficult to decide on the vacuum hole diameter, 6b in FIG. 1 of the '678 patent. If the hole is large, small stones will immediately get sucked upwards into the vacuum line. If the hole is small, stone holding is weak and unreliable, and the vacuum line can easily become clogged by sucking in a grain of foreign matter. With regard to the source of the vacuum, this may be available in a lapidary location, but in other locations a portable vacuum pump would be needed to operate the device.

In contradistinction thereto, the present invention does not require a vacuum connection for its operation. Stone clamping is mechanical, reliable and is suitable for stones of any size within the intended range of the device. The device can be manufactured as a portable item, which is important to salespeople who need to travel, as most locations do not provide a vacuum connection.

It will thus be realized that the novel device of the present invention by utilizing frequency measurements which are very sensitive to the mass suspended on a vibrating body, can produce results superior to those available from electronic scales, particularly when weighing small stones in the 0.2–0.5 carat range.

The device includes a commercially available microprocessor which is programmed to handle the sequencing of the measurement and translates the change in frequency to grams, carats or points and drives a results display as required.

The sensitivity of the device is further enhanced by arranging for the forceps to be of minimum possible weight, so that the addition of a stone held thereby brings about the largest possible decrease in vibration frequency.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a and 3b are schematic views of an embodiment using piezoelectric elements;

FIG. 4 is an elevational view of a further embodiment of the forceps;

FIG. 5 is a detail view showing forceps arms terminating in an object location form;

FIG. 6 is a detail view of the forceps seen in FIG. 1 gripping a diamond;

Figure 1:
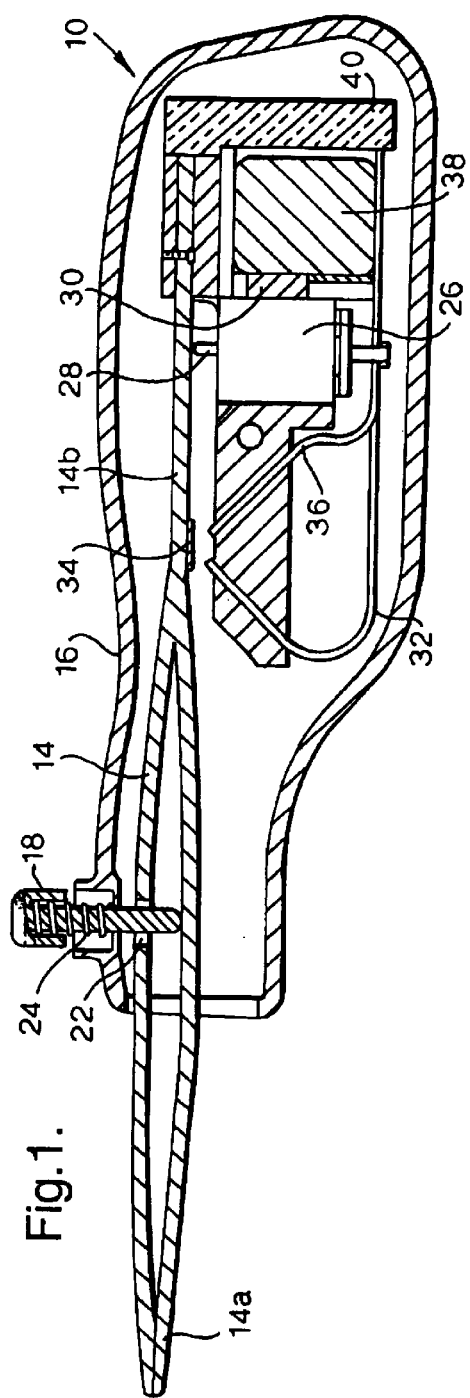
FIG. 1 is a sectional elevation view of a preferred embodiment of the weighing apparatus according to the invention, using an optical system to measure vibration frequency.

There is seen in FIG. 1 a fully portable self-contained embodiment of an apparatus 10 for measuring the mass and calculating the weight of a small object 12, seen in FIG. 3a. The object 12 can be held in the proximal portion 14a of the forceps 14 extending beyond the housing 16. The distal portion 14b of the forceps 14, the means for initiating vibration thereof and the means for measuring the oscillating frequency of the forceps 14 while the object 12 is held thereby are all contained in the unitary hand-holdable housing 16.

The housing 16 supports forceps actuating means 18 which interact with the forceps 14 for opening the proximal portion 14a to allow insertion of the object 12, seen in FIG. 3a which is to be weighed. Pressure on the actuating means 18 allows the forceps 14 to grasp the object to be weighed. The actuating means 18 comprise a headed pin passing through a surface of the housing 16 and through an aperture 22. The button head of means 18 is pushable against spring bias 24 to separate the arms of the forceps 14.

Vibration of the forceps 14 is initiated by application of a momentary electric pulse to a solenoid 26, causing the solenoid plunger 28 to strike the forceps 14.

An optical system is used to measure vibration frequency. A light emitter and receiver unit 30 including a LED (Light Emitting Diode) provides a light beam which is conveyed by a first optical fiber 32 to impinge on a reflective area 34 of the vibrating forceps 14. In the present embodiment a the reflective area 34 is a mirror attached underneath the forceps 14. The mirror vibrates together with the forceps 14, and consequently reflects light received into a second optical fiber 36 only when suitably aligned during a portion of its vibrational movement. Thus the second optical fiber 36 receives an intermittent light signal which it conveys to the emitter-receiver unit 30. The unit 30 arranged to measure the time between light pulses, which information is passed on electronically to the microprocessor 38 for calculating the vibration frequency.

A battery 40 removably held in the housing 16 provides all the power needed to allow cordless operation.

With regard to the rest of the figures, similar reference numerals have been used to identify similar parts.

Figure 2:
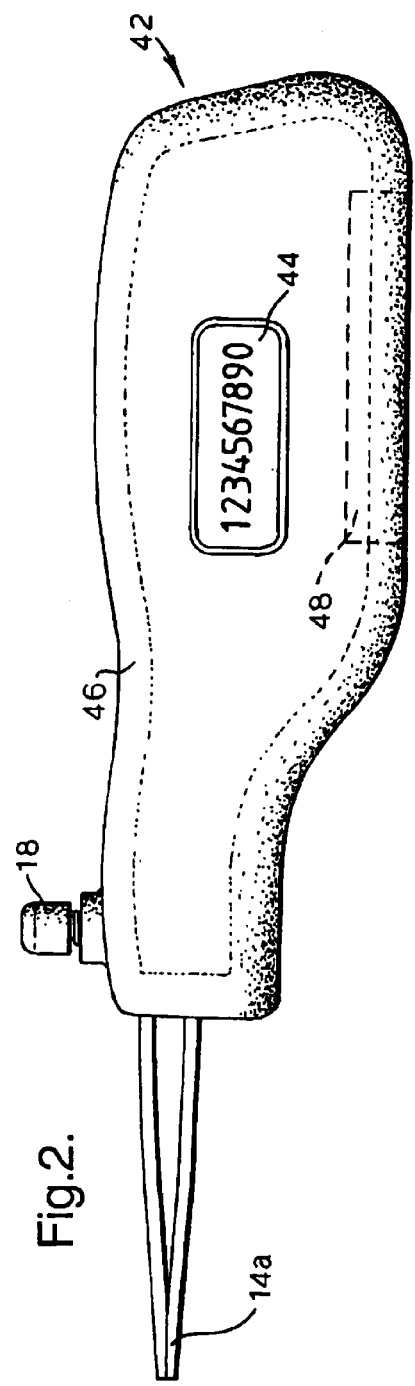
FIG. 2 is an elevational view of an embodiment similar to FIG. 1, including an integral results display.

Seen in FIG. 2 is an apparatus 42 similar to 10 seen in the previous figure. The apparatus 42 further comprises integral display means 44, such as a LCD (Liquid Crystal Display), for showing the computed weight of an object to be held thereby. A housing 46 also holds a power management unit 48 to reduce power demand to the minimum necessary and to turn power off a few minutes after the device becomes idle.

Referring now to FIGS. 3a and 3b there is seen a further embodiment 52 of the apparatus for measuring the mass and calculating the weight of small objects 12. A housing 54 envelopes means for oscillating the forceps 56, in the present embodiment piezoelectric transmitter 60, and a piezoelectric detector 58, which translates pressure waves into an electric signal to report frequency to the microprocessor 62. The distal portion 56a of the forceps 56 is rigidly attached within the housing 54. The forceps 56 are held normally open by a spring 58 and headed pin 68, as seen in FIG. 2b, and are closed by the user applying finger pressure to a button 64. Electric power is received through a flexible cable 66.

Referring now to FIG. 4, there is depicted an embodiment of the forceps 70 which can be used in the apparatus for measuring the mass and calculating the weight of objects. The forceps 70 comprise a proximal portion formed of two arms 74 adapted to be displaced relative to each other against a bending bias and thereby to grasp and hold the object 72 to be weighed. A distal portion 76 of the forceps is seen as a solid body on the right side of the figure. The solid body provides a good base for the arms 74 as it is substantially unaffected by the vibration thereof, and can be easily attached to a housing, for example 16 of FIG. 1. The arms 74 and the solid distal portion 76 of the forceps are formed as an integral unit. The base 78 of the arms 74 is formed to be thin in order to ensure that the vibration thereof will be rooted at this defined point.

The arms 74 may be opened by a non-circular cam-like eccentric body (not shown) inserted between the arms 74, the non-circular body being rotatable by about 90°.

The forceps 70 can be manufactured by machining, investment casting or powder metallurgy.

FIG. 5 shows a detail of a further embodiment of forceps 80 which can be used in an apparatus for measuring the mass and calculating the weight of an object 82, which is shown as a gemstone in the figure. The forceps arms 84 terminate in an object-location element 86. The V form of the object-location element 86 ensures that grasped objects 82 are held at a fixed distance from the distal portion (not seen) of the forceps 80. Correct positioning of the object 82 to be weighed is important in obtaining accurate results.

FIG. 6 illustrates the forward part of the weighing apparatus 10 previously seen in FIG. 1, the proximate portion 14a of the forceps 14 being seen holding a polished diamond 88.

Figure 7:
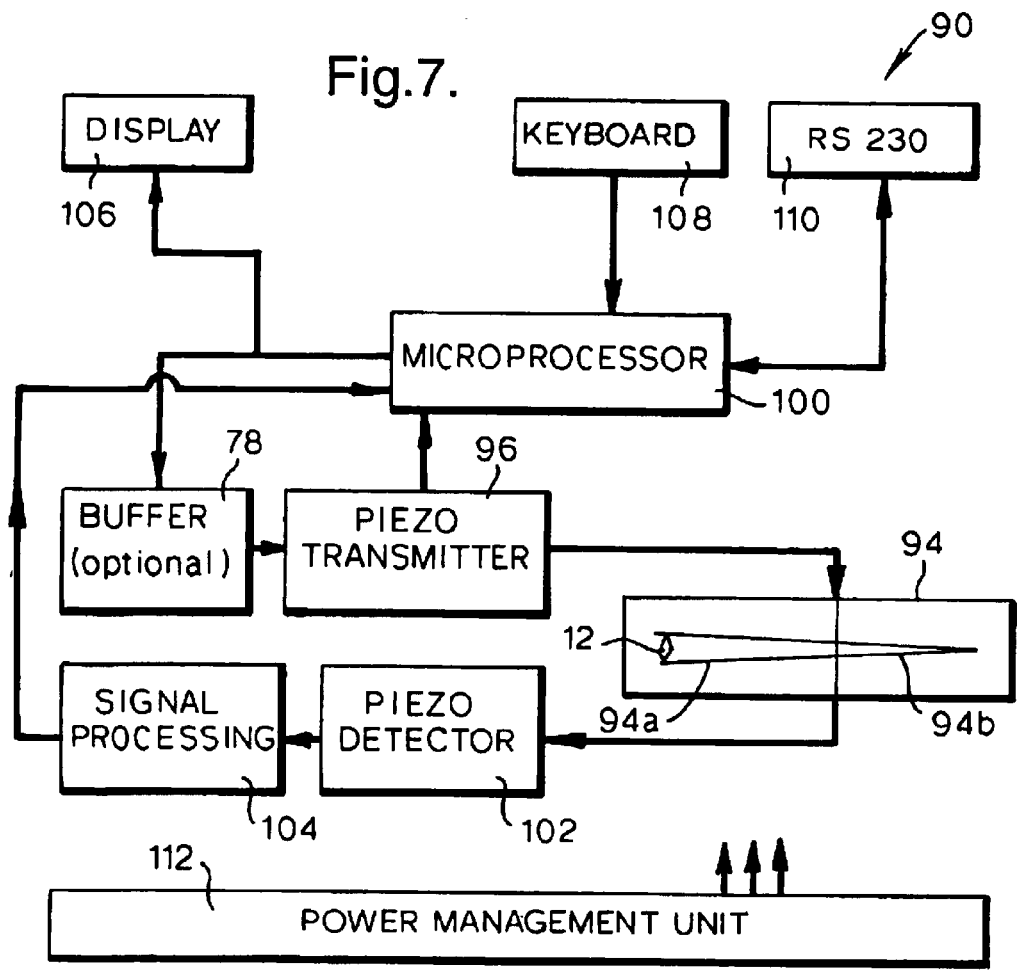
FIG. 7 is a block diagram of an embodiment including means for inputting data.

In FIG. 7 a block diagram represents an apparatus 90 for measuring the mass and calculating the weight of individual objects 12 to be held thereby.

The selected object 12 is mechanically held by forceps 94 having a proximal portion 94a and a distal portion 94b. The proximal portion 94a is adapted to grasp and hold the object 12.

Piezoelectric vibration generating means 96 contact the forceps 94 for initiating vibration thereof while the object 12 is held thereby. Optionally a buffer 98 is inserted between a microprocessor 100 which controls the apparatus 90 and the Piezoelectric vibration generating means 96. Piezoelectric detector means 102 measures the oscillating frequency of the forceps 94 while the object 12 is held thereby. The measured higher oscillating frequency of the empty forceps 94 is previously stored in the microprocessor memory and is now used to compute the mass and the weight of the object 12. After signal processing 104 the results are displayed, for example on the screen 106 of a connected computer.

Alternatively, the device of the present invention can be provided with known per se IRDA wireless technology means for transmitting the results to a separate computer device.

Optionally the microprocessor 100 is connected to a keyboard 108 and a RS232 connector 110 for effecting any desired changes in operation.

If the power source is a battery 40, as seen in FIG. 1, a power management unit 112 is added to reduce power demand to the minimum necessary and to turn power off a few minutes after the device becomes idle.

Figure 8:
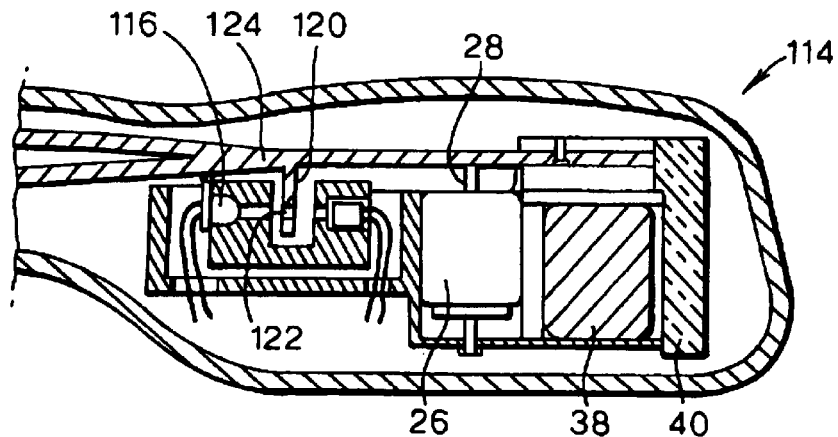
FIG. 8 is a sectional elevation view of part of a further preferred embodiment of the weighing apparatus using an optical system to measure vibration frequency.

Referring now to FIG. 8, there is seen a portion of a further preferred embodiment 114 of the weighing apparatus using an optical system to measure vibration frequency.

A light source 116, such as the miniaturized Light Emitting Diode (LED) seen in the figure radiates light towards a light detector 118. A mask element 120 pierced by a pinhole aperture 122 is supported by forceps 124 and is disposed between the light source 116 and the detector 118. Vibration of the forceps 124 results in light reaching the detector 118 intermittently, and generating a corresponding detector electrical output which is passed on to the microprocessor 38.

Similarly to the arrangement seen in FIG. 1, vibration of the forceps 124 is initiated by application of a momentary electric pulse to a solenoid 26, causing the solenoid plunger 28 to strike the forceps 124.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An apparatus for measuring the mass and calculating the weight of individual objects to be held thereby, comprising forceps having a proximal portion and a distal portion, said proximal portion being adapted to grasp and hold a selected object, means associated with said forceps for initiating vibration of the same while said object is held thereby and means for measuring the oscillating frequency of said forceps while said object is held thereby, and for utilizing the measured higher oscillating frequency of the empty forceps to compute the mass and the weight of said selected object.

2. An apparatus for measuring the mass and calculating the weight of objects, according to claim 1, further comprising a housing enveloping at least said means for oscillating and said measuring means.

3. An apparatus for measuring the mass and calculating the weight of objects, according to claim 2, wherein said proximal portion of said forceps extends beyond said housing and wherein said apparatus further comprises actuating means interacting with said forceps for opening the same for grasping purposes.

4. An apparatus for measuring the mass and calculating the weight of objects, according to claim 3, wherein said actuating means comprise a headed pin passing through a surface of said housing and pushable against spring bias to separate the arms of said forceps.

5. An apparatus for measuring the mass and calculating the weight of objects, according to claim 1, wherein said means for initiating vibration of said forceps are solenoid means.

6. An apparatus for measuring the mass and calculating the weight of objects, according to claim 1, wherein said means for measuring the oscillating frequency of said forceps include optical means.

7. An apparatus for measuring the mass and calculating the weight of objects, according to claim 6, wherein said optical means include a light emitter, a light detector and a plurality of optical fibers adapted to transfer light to the vibrating forceps and to transfer collected light inputs to said detector.

8. An apparatus for measuring the mass and calculating the weight of objects, according to claim 1, wherein said forceps, said means for initiating vibration thereof and said means for measuring the oscillating frequency of said forceps while said object is held thereby are all contained in a unitary hand-holdable housing further comprising display means for showing the computed weight of said object held thereby.

9. An apparatus for measuring the mass and calculating the weight of objects, according to claim 8, further including an electric power source for cordless operation.

10. An apparatus for measuring the mass and calculating the weight of objects, according to claim 2, wherein said distal portion of said forceps is rigidly attached within said housing.

11. An apparatus for measuring the mass and calculating the weight of objects, according to claim 1, wherein said forceps comprise a proximal portion formed of two arms adapted to be displaced relative to each other against a bending bias and thereby to grasp and hold a selected object, and a distal portion wherein said arms and portions of said forceps are formed as an integral unit.

12. An apparatus for measuring the mass and calculating the weight of objects, according to claim 1, wherein said proximal portion of said forceps are provided with an object-location element ensuring that grasped objects are held at a fixed distance from said distal portion of said forceps.

13. An apparatus for measuring the mass and calculating the weight of objects, according to claim 1, wherein said object is a gemstone.

14. An apparatus for measuring the mass and calculating the weight of objects, according to claim 1, wherein said means for initiating vibration of said forceps are solenoid means.

15. An apparatus for measuring the mass and calculating the weight of objects, according to claim 1, wherein said object is a diamond.

* * * * *